United States Patent
Zhang et al.

(10) Patent No.: US 11,623,204 B2
(45) Date of Patent: Apr. 11, 2023

(54) METHOD FOR PREPARING MODIFIED CELLULOSE AEROGEL FOR GLYCOPROTEIN SEPARATION

(71) Applicant: Shaanxi University of Science & Technology, Xi'an (CN)

(72) Inventors: Sufeng Zhang, Xi'an (CN); Xue Yao, Xi'an (CN); Liwei Qian, Xi'an (CN); Chen Hua, Xi'an (CN); Ning Wei, Xi'an (CN); Quansheng Wang, Xi'an (CN)

(73) Assignee: Shaanxi University of Science & Technology, Xi'an (CN)

( * ) Notice: Subject to any disclaimer, the term of this patent is extended or adjusted under 35 U.S.C. 154(b) by 37 days.

(21) Appl. No.: 17/470,240

(22) Filed: Sep. 9, 2021

(65) Prior Publication Data

US 2022/0080384 A1 Mar. 17, 2022

(30) Foreign Application Priority Data

Sep. 16, 2020 (CN) .......................... 202010975603.9

(51) Int. Cl.
| | |
|---|---|
| *B01J 20/24* | (2006.01) |
| *B01J 20/28* | (2006.01) |
| *B01J 20/30* | (2006.01) |
| *C07K 1/14* | (2006.01) |
| *C08B 15/06* | (2006.01) |
| *C08B 16/00* | (2006.01) |
| *C08J 9/28* | (2006.01) |
| *C08L 1/02* | (2006.01) |

(52) U.S. Cl.
CPC ......... *B01J 20/24* (2013.01); *B01J 20/28047* (2013.01); *B01J 20/305* (2013.01); *B01J 20/3071* (2013.01); *B01J 20/3085* (2013.01); *C07K 1/145* (2013.01); *C08B 15/06* (2013.01); *C08B 16/00* (2013.01); *C08J 9/283* (2013.01); *C08L 1/02* (2013.01); *C08J 2201/0484* (2013.01); *C08J 2205/026* (2013.01); *C08J 2301/02* (2013.01)

(58) Field of Classification Search
CPC .... B01J 20/24; B01J 20/28047; B01J 20/305; B01J 20/3071; B01J 20/3085; B01J 20/30; C08J 2205/026; C08J 2205/02; C08J 2301/02; C08J 9/36; C08J 2301/08; C08J 9/28; C08J 2201/0484; C08L 1/02; C08L 1/08; C08B 15/10; C08B 16/00; C08B 15/06
USPC ........................................................ 502/307
See application file for complete search history.

(56) References Cited

FOREIGN PATENT DOCUMENTS

| CN | 107141504 A | * | 9/2017 | |
|---|---|---|---|---|
| CN | 108238595 A | * | 7/2018 | .............. B01J 13/00 |
| CN | 109908878 A | * | 6/2019 | |

OTHER PUBLICATIONS

Machine translation of CN 108238595 A originally published Jul. 2018 to Lu et al. (Year: 2018).*
Machine translation of CN 109908878 A originally published Jun. 2019 to Liu et al. (Year: 2019).*
Erlandsson et al., On the mechanism behind freezing-induced chemical crosslinking in ice-templated cellulose nanofibril aerogels, J. Mater. Chem. A, 2018, 6, 193711-19380 (Year: 2018).*
Machine translation of CN 107141504 A originally published Sep. 2017 to Lin et al. (Year: 2017).*
Xiang et al., A highly recyclable dip-catalyst produced from palladium nanoparticle-embedded bacterial cellulose and plant fibers, 2018, vol. 20, pp. 1085-1094 (Year: 2018).*

* cited by examiner

*Primary Examiner* — Stefanie J Cohen
*Assistant Examiner* — Ritu S Shirali
(74) *Attorney, Agent, or Firm* — Offit Kurman. P.A.; Chintan A. Desai

(57) ABSTRACT

A method for preparing a modified cellulose aerogel for glycoprotein separation is provided. In this method, cellulose aerogel is employed as a substrate. The cellulose aerogel is known to have a three-dimensional network structure with extremely high porosity and specific surface area and extremely low density. So, by using the cellulose aerogel as a substrate, it is possible to provide the glycoproteins to be separated with more binding sites. PEI dendrimer has abundant functional groups and can easily be modified. By modifying the cellulose aerogel substrate with the PEI dendrimer, it is possible to improve the density of the phenylboronic acid bound to the substrate, thereby leading to higher affinity toward the glycoproteins to be separated.

6 Claims, No Drawings

METHOD FOR PREPARING MODIFIED CELLULOSE AEROGEL FOR GLYCOPROTEIN SEPARATION

CROSS-REFERENCE TO RELATED APPLICATIONS

The present application claims priority to and the benefit of Chinese Patent Application No. 202010975603.9 filed on Sep. 16, 2020, the disclosure of which is incorporated by reference herein in its entirety as part of the present application.

TECHNICAL FIELD

The present disclosure relates generally to the field of glycoprotein separation, and in particular, to a method for preparing a modified cellulose aerogel for glycoprotein separation.

BACKGROUND

Protein glycosylation is critical for a wide range of biological processes including immune response and protein folding. Alterations in structure and configuration of sugar chains contained in glycoproteins have been shown to be associated with disease development and progression. For instance, a lot of abnormal glycoproteins are found in patients with tumor or cancer. Glycoproteins are thought to be an important biomarker and therapeutic target, and are also often used for the diagnosis of a disease. However, the abundance of glycoproteins is low in complex biological samples or clinical samples, so it is important to separate and enrich the glycoproteins from the samples.

Common materials currently used for glycoprotein separation include organic and inorganic monolithic materials, and magnetic materials. However, the organic monolithic materials disadvantageously have poor mechanical stability and poor stability toward swelling by organic solvents. These materials also have disadvantages of low specific surface area and permeability. The inorganic monolithic materials require a complex, multistep manufacturing process, and are also pH sensitive. Particles of the magnetic materials tend to agglomerate in solvents and exhibit very poor dispersibility, due to their strong magnetism and dipole-dipole interaction forces between the molecules. Also, the magnetic materials disadvantageously have biological toxicity.

Celluloses, as a natural polymer that is hydrophilic in nature, can be obtained from a vast variety of natural resources. Furthermore, celluloses are non-toxic and have good biocompatibility, and have been widely used in the biomedical field. Aerogels are a porous material having a three-dimensional network structure with extremely high porosity and specific surface area and extremely low density. Aerogels have been widely used in the field of separation technology due to their unique physical structure and characteristics. Cellulose-based aerogels or cellulose aerogels have attracted much attention as a substrate used for the separation of glycoproteins via a boronic acid-based approach, which utilizes reversible covalent binding between boronic acids and cis-diol groups of the glycoproteins. In particular, when the pH of the surrounding solution is basic, the boronic acid presents as the form of a tetragonal boronate anion ($sp^3$), which can be esterified with the cis-diol groups to form covalent bonds therebetween; while when the surrounding pH becomes acidic, the boronic acid presents as a trigonal configuration ($sp^2$) and the binding between the $sp^2$ form of the boronic acid and the cis-diol groups substantially decreased. With this approach, it is therefore possible to achieve rapid, low cost, and effective separation of glycoproteins simply through pH adjustment in an environmentally friendly manner. For these reasons, cellulose aerogels are widely used for separation of glycoproteins.

SUMMARY

An objective of the present disclosure is to provide a method for preparing a modified cellulose aerogel for glycoprotein separation, the modified cellulose aerogel having an increased density of phenylboronic acid ligands, thereby leading to higher affinity toward glycoproteins to be separated and thus to effective separation thereof.

Accordingly, the objective of the present disclosure is realized by a method for preparing a modified cellulose aerogel for glycoprotein separation, comprising steps of:

(1) adding sodium hydroxide (NaOH) and urea to deionized water and stirring to form a first solution, which is pre-cooled at −12.5° C.;

(2) into the pre-cooled first solution, cellulose is added and completely dissolved and then a volume of 2 to 5 mL of epichlorohydrin (ECH) is added to form a second solution, which is poured into a mould and allowed to stand for 24 h and is then washed and freeze dried to obtain a regenerated cellulose aerogel;

(3) adding the regenerated cellulose aerogel obtained in the step (2) and sodium periodate ($NaIO_4$) to deionized water and stirring to form a third solution, which is subjected to a reaction in the dark at a temperature of 50 to 70° C. for 5 to 7 h, at the end of which time a volume of 3 to 5 mL of ethylene glycol is added and stirred for 30 to 60 min followed by washing with deionized water and ethanol and then freeze drying to obtain a dialdehyde cellulose aerogel;

(4) adding the dialdehyde cellulose aerogel obtained in the step (3) to anhydrous ethanol to form a fourth solution, to which polyethyleneimine (PEI) and sodium cyanoborohydride ($CH_3BNNa$) are added to conduct a reaction at a temperature of 50 to 70° C. for 6 h followed by washing with ethanol to neutral and then freeze drying to obtain a PEI-modified cellulose aerogel; and (5) dissolving 4-formylphenylboronic acid in a volume of 100 to 500 mL of anhydrous ethanol to form a fifth solution, to which the PEI-modified cellulose aerogel obtained in the step (4) and sodium cyanoborohydride ($NaCNBH_3$) are added to conduct a reaction at 50° C. for 12 to 24 h followed by washing with distilled water and ethanol and then vacuum drying to obtain a PEI/phenylboronic acid (PBA)-modified cellulose aerogel.

In some embodiments, in the step (1), the NaOH, urea, and deionized water are employed in an amount of 6 to 10 g, 9 to 13 g, and 77 to 85 mL, respectively.

In some embodiments, in the step (2), the cellulose is employed in an amount of 2 to 5 g.

In some embodiments, in the step (3), the molar ratio of $NaIO_4$ to the regenerated cellulose aerogel is in a range of 1 to 1.5, and the deionized water is employed in an amount of 150 to 500 mL.

In some embodiments, in the step (4), the dialdehyde cellulose aerogel, anhydrous ethanol, PEI, and $CH_3BNNa$ are employed in an amount of 1 to 1.5 g, 50 to 200 mL, 2.7 to 4.5 g, and 3 to 5 g, respectively.

In some embodiments, in the step (5), the 4-formylphenylboronic acid, anhydrous ethanol, PEI-modified cellulose aerogel, and NaCNBH$_3$ are employed in an amount of 3 to 5 g, 100 to 500 mL, 1 to 3 g, and 5 to 8 g, respectively.

In the method of the disclosure, cellulose aerogel is employed as a substrate. The cellulose aerogel is known to have a three-dimensional network structure with extremely high porosity and specific surface area and extremely low density, as mentioned in the background. So, by using the cellulose aerogel as a substrate, it is possible to provide the glycoproteins to be separated with more binding sites. PEI dendrimer has abundant functional groups and can easily be modified. By modifying the cellulose aerogel substrate with the PEI dendrimer, it is possible to improve the density of the phenylboronic acid bound to the substrate, thereby leading to higher affinity toward the glycoproteins to be separated.

DETAILED DESCRIPTION OF ILLUSTRATIVE EMBODIMENTS

The disclosure will now be described further by way of examples.

In an embodiment, a method for preparing a modified cellulose aerogel for glycoprotein separation, comprising steps of:

(1) adding 6 to 10 g of NaOH and 9 to 13 g of urea to a volume of 77 to 85 mL of deionized water and stirring to form a first solution, which is pre-cooled at −12.5° C.;

(2) into the pre-cooled first solution, 2 to 5 g of cellulose (cotton linter pulp, DP=600, with α-cellulose content of above 95%) is added with vigorous stirring and completely dissolved and then a volume of 2 to 5 mL of ECH is added to form a second solution, which is poured into a mould and allowed to stand for 24 h and is then washed and freeze dried to obtain a regenerated cellulose aerogel (R-CA);

(3) adding 1 mol of the R-CA and 1 to 1.5 mol of NaIO$_4$ to a volume of 150 to 500 mL of deionized water and stirring to form a third solution, which is subjected to a reaction in the dark at a temperature of 50 to 70° C. for 5 to 7 h, at the end of which time a volume of 3 to 5 mL of ethylene glycol is added and stirred for 30 to 60 min followed by washing with deionized water and ethanol and then freeze drying to obtain a dialdehyde cellulose aerogel (D-CA);

(4) adding 1 to 1.5 g of the D-CA to a volume of 50 to 200 mL of anhydrous ethanol to form a fourth solution, to which 2.7 to 4.5 g of PEI and 3 to 5 g of CH$_3$BNNa are added to conduct a reaction at a temperature of 50 to 70° C. for 6 h followed by washing with a large amount of ethanol to neutral and then freeze drying to obtain a PEI-modified cellulose aerogel (PEI-CA); and (5) dissolving 3 to 5 g of 4-formylphenylboronic acid in a volume of 100 to 500 mL of anhydrous ethanol to form a fifth solution, to which 1 to 3 g of the PEI-CA and 5 to 8 g of NaCNBH$_3$ are added to conduct a reaction at 50° C. for 12 to 24 h followed by washing with distilled water and ethanol and then vacuum drying to obtain a PEI/PBA-modified cellulose aerogel (PEI-PBA-CA).

Example 1

6 g of NaOH and 9 g of urea were added to 85 mL of deionized water and well stirred to form a first solution. The first solution was then pre-cooled at −12.5° C.

2 g of cotton linter pulp was added to the pre-cooled first solution with vigorous stirring and completely dissolved therein. Thereto was added 2 mL of ECH to form a uniform second solution by stirring. The second solution was poured into a mould and allowed to stand for 24 h, followed by washing and freeze drying to obtain R-CA.

1 mol of the R-CA and 1 mol of NaIO$_4$ were added to 150 mL of deionized water and well stirred to form a third solution. The third solution was subjected to a reaction in the dark at 50° C. for 5 h. At the end of the reaction, 3 mL of ethylene glycol was added to the reaction mixture and stirred for 30 min. The resulting reaction product was washed with deionized water and ethanol and then freeze dried to obtain D-CA.

1 g of the D-CA was added to 50 mL of anhydrous ethanol to form a fourth solution. 2.7 g of PEI and 3 g of CH$_3$BNNa were added thereto to conduct a reaction at 50° C. for 6 h. The reaction product was washed with a large amount of ethanol to neutral and then freeze dried to obtain PEI-CA.

3 g of 4-formylphenylboronic acid was dissolved in 100 mL of anhydrous ethanol to form a fifth solution. 1 g of the PEI-CA and 5 g of NaCNBH$_3$ were added thereto to conduct a reaction at 50° C. for 12 h. The reaction product was washed with distilled water and ethanol and then vacuum dried to obtain PEI/PBA-CA.

Example 2

7 g of NaOH and 12 g of urea were added to 81 mL of deionized water and well stirred to form a first solution. The first solution was then pre-cooled at −12.5° C.

3 g of cotton linter pulp was added to the pre-cooled first solution with vigorous stirring and completely dissolved therein. Thereto was added 2 mL of ECH to form a uniform second solution by stirring. The second solution was poured into a mould and allowed to stand for 24 h, followed by washing and freeze drying to obtain R-CA.

1 mol of the R-CA and 1.1 mol of NaIO$_4$ were added to 200 mL of deionized water and well stirred to form a third solution. The third solution was subjected to a reaction in the dark at 70° C. for 5 h. At the end of the reaction, 4 mL of ethylene glycol was added to the reaction mixture and stirred for 60 min. The resulting reaction product was washed with deionized water and ethanol and then freeze dried to obtain D-CA.

1.5 g of the D-CA was added to 150 mL of anhydrous ethanol to form a fourth solution. 4.0 g of PEI and 5 g of CH$_3$BNNa were added thereto to conduct a reaction at 70° C. for 6 h. The reaction product was washed with a large amount of ethanol to neutral and then freeze dried to obtain PEI-CA.

3 g of 4-formylphenylboronic acid was dissolved in 300 mL of anhydrous ethanol to form a fifth solution. 3 g of the PEI-CA and 8 g of NaCNBH$_3$ were added thereto to conduct a reaction at 50° C. for 24 h. The reaction product was washed with distilled water and ethanol and then vacuum dried to obtain PEI/PBA-CA.

Example 3

10 g of NaOH and 9 g of urea were added to 81 mL of deionized water and well stirred to form a first solution. The first solution was then pre-cooled at −12.5° C.

4 g of cotton linter pulp was added to the pre-cooled first solution with vigorous stirring and completely dissolved therein. Thereto was added 5 mL of ECH to form a uniform second solution by stirring. The second solution was poured into a mould and allowed to stand for 24 h, followed by washing and freeze drying to obtain R-CA.

1 mol of the R-CA and 1.5 mol of NaIO$_4$ were added to 300 mL of deionized water and well stirred to form a third solution. The third solution was subjected to a reaction in the dark at 70° C. for 7 h. At the end of the reaction, 5 mL of ethylene glycol was added to the reaction mixture and stirred for 60 min. The resulting reaction product was washed with deionized water and ethanol and then freeze dried to obtain D-CA.

1.5 g of the D-CA was added to 200 mL of anhydrous ethanol to form a fourth solution. 2.7 g of PEI and 4.5 g of $CH_3BNNa$ were added thereto to conduct a reaction at 50° C. for 6 h. The reaction product was washed with a large amount of ethanol to neutral and then freeze dried to obtain PEI-CA.

4 g of 4-formylphenylboronic acid was dissolved in 450 mL of anhydrous ethanol to form a fifth solution. 2.5 g of the PEI-CA and 6 g of $NaCNBH_3$ were added thereto to conduct a reaction at 50° C. for 12 h. The reaction product was washed with distilled water and ethanol and then vacuum dried to obtain PEI/PBA-CA.

Example 4

10 g of NaOH and 10 g of urea were added to 80 mL of deionized water and well stirred to form a first solution. The first solution was then pre-cooled at −12.5° C.

5 g of cotton linter pulp was added to the pre-cooled first solution with vigorous stirring and completely dissolved therein. Thereto was added 5 mL of ECH to form a uniform second solution by stirring. The second solution was poured into a mould and allowed to stand for 24 h, followed by washing and freeze drying to obtain R-CA.

1 mol of the R-CA and 1.3 mol of $NaIO_4$ were added to 500 mL of deionized water and well stirred to form a third solution. The third solution was subjected to a reaction in the dark at 70° C. for 7 h. At the end of the reaction, 5 mL of ethylene glycol was added to the reaction mixture and stirred for 30 min. The resulting reaction product was washed with deionized water and ethanol and then freeze dried to obtain D-CA.

1.2 g of the D-CA was added to 100 mL of anhydrous ethanol to form a fourth solution. 3.5 g of PEI and 3.5 g of $CH_3BNNa$ were added thereto to conduct a reaction at 70° C. for 6 h. The reaction product was washed with a large amount of ethanol to neutral and then freeze dried to obtain PEI-CA.

4.5 g of 4-formylphenylboronic acid was dissolved in 100 to 500 mL of anhydrous ethanol to form a fifth solution. 3 g of the PEI-CA and 7.5 g of $NaCNBH_3$ were added thereto to conduct a reaction at 50° C. for 24 h. The reaction product was washed with distilled water and ethanol and then vacuum dried to obtain PEI/PBA-CA.

Example 5

6 g of NaOH and 13 g of urea were added to 81 mL of deionized water and well stirred to form a first solution. The first solution was then pre-cooled at −12.5° C.

4 g of cotton linter pulp was added to the pre-cooled first solution with vigorous stirring and completely dissolved therein. Thereto was added 3.5 mL of ECH to form a uniform second solution by stirring. The second solution was then poured into a mould and allowed to stand for 24 h, followed by washing and freeze drying to obtain R-CA.

1 mol of the R-CA and 1.1 mol of $NaIO_4$ were added to 350 mL of deionized water and well stirred to form a third solution. The third solution was subjected to a reaction in the dark at 65° C. for 7 h. At the end of the reaction, 5 mL of ethylene glycol was added to the reaction mixture and stirred for 60 min. The resulting reaction product was washed with deionized water and ethanol and then freeze dried to obtain D-CA.

1 g of the D-CA was added to 50 to 200 mL of anhydrous ethanol to form a fourth solution. 4.5 g of PEI and 5 g of $CH_3BNNa$ were added thereto to conduct a reaction at 70° C. for 6 h. The reaction product was washed with a large amount of ethanol to neutral and then freeze dried to obtain PEI-CA.

5 g of 4-formylphenylboronic acid was dissolved in 500 mL of anhydrous ethanol to form a fifth solution. 2.5 g of the PEI-CA and 6 g of $NaCNBH_3$ were added thereto to conduct a reaction at 50° C. for 24 h. The reaction product was washed with distilled water and ethanol and then vacuum dried to obtain PEI/PBA-CA.

The method of the disclosure provides at least the following advantages.

First, the method is simple and environmentally safe, and the materials used by this method have good biocompatibility.

Next, the use of PEI to modify the cellulose aerogel substrate can improve the selectivity and identification capability of the phenylboronic acid to be bound to the substrate for glycoproteins, and thus improve its separation capability of separating the glycoproteins from the complex biological samples or clinical samples.

Further, with the PEI/PBA-CA prepared by the present method, it is possible to achieve simple and effective separation of glycoproteins. In the glycoprotein separation using the PEI/PBA-CA, as mentioned in the background, when the pH of the surrounding solution is basic, the boronic acid presents as the form of a tetragonal boronate anion ($sp^3$), which can be esterified with the cis-diol groups of the glycoproteins to form covalent bonds therebetween; while when the surrounding pH becomes acidic, the boronic acid presents as a trigonal configuration ($sp^2$), resulting in dissociation of the ester.

What is claimed is:

1. A method for preparing a modified cellulose aerogel for glycoprotein separation, comprising steps of:
   (1) adding sodium hydroxide and urea to deionized water and stirring to form a first solution, which is pre-cooled at −12.5° C.;
   (2) into the pre-cooled first solution, cellulose is added and completely dissolved and then a volume of 2 to 5 mL of epichlorohydrin is added to form a second solution, which is poured into a mould and allowed to stand for 24 h and is then washed and freeze dried to obtain a regenerated cellulose aerogel;
   (3) adding the regenerated cellulose aerogel obtained in the step (2) and sodium periodate to deionized water and stirring to form a third solution, which is subjected to a reaction in the dark at a temperature of 50 to 70° C. for 5 to 7 h, at the end of which time a volume of 3 to 5 mL of ethylene glycol is added and stirred for 30 to 60 min followed by washing with deionized water and ethanol and then freeze drying to obtain a dialdehyde cellulose aerogel;
   (4) adding the dialdehyde cellulose aerogel obtained in the step (3) to anhydrous ethanol to form a fourth solution, to which polyethyleneimine (PEI) and sodium cyanoborohydride are added to conduct a reaction at a temperature of 50 to 70° C. for 6 h followed by washing with ethanol to neutral and then freeze drying to obtain a PEI-modified cellulose aerogel; and
   (5) dissolving 4-formylphenylboronic acid in a volume of 100 to 500 mL of anhydrous ethanol to form a fifth solution, to which the PEI-modified cellulose aerogel obtained in the step (4) and sodium cyanoborohydride are added to conduct a reaction at 50° C. for 12 to 24 h followed by washing with distilled water and ethanol and then vacuum drying to obtain a PEI/phenylboronic acid (PBA)-modified cellulose aerogel.

2. The method of claim 1, wherein, in the step (1), the sodium hydroxide, urea, and deionized water are employed in an amount of 6 to 10 g, 9 to 13 g, and 77 to 85 mL, respectively.

3. The method of claim 1, wherein, in the step (2), the cellulose is employed in an amount of 2 to 5 g.

4. The method of claim 1, wherein, in the step (3), a molar ratio of sodium periodate to the regenerated cellulose aerogel is in a range of 1 to 1.5, and the deionized water is employed in an amount of 150 to 500 mL.

5. The method of claim 1, wherein, in the step (4), the dialdehyde cellulose aerogel, anhydrous ethanol, polyethyleneimine, and sodium cyanoborohydride are employed in an amount of 1 to 1.5 g, 50 to 200 mL, 2.7 to 4.5 g, and 3 to 5 g, respectively.

6. The method of claim 1, wherein, in the step (5), the 4-formylphenylboronic acid, anhydrous ethanol, PEI-modified cellulose aerogel, and sodium cyanoborohydride are employed in an amount of 3 to 5 g, 100 to 500 mL, 1 to 3 g, and 5 to 8 g, respectively.

\* \* \* \* \*